United States Patent [19]

Starck et al.

[11] Patent Number: 4,741,731
[45] Date of Patent: May 3, 1988

[54] VENTED ULTRASONIC TRANSDUCER FOR SURGICAL HANDPIECE

[75] Inventors: Brent R. Starck, Gurnee; Joseph F. Brumbach, Niles; Robert F. Zapka, Berwyn, all of Ill.

[73] Assignee: Fibra-Sonics, Inc., Chicago, Ill.

[21] Appl. No.: 830,752

[22] Filed: Feb. 19, 1986

[51] Int. Cl.[4] .................... A61B 17/32; A61L 33/00; A61H 23/02
[52] U.S. Cl. .................................. 604/22; 128/24 A; 310/323
[58] Field of Search ................. 128/24 A, 36; 604/22; 310/327, 334

[56] References Cited

U.S. PATENT DOCUMENTS

| | | | |
|---|---|---|---|
| 2,283,285 | 5/1942 | Pohlman | 310/327 |
| 2,412,093 | 12/1946 | Mininberg | 128/36 |
| 3,589,363 | 6/1971 | Banko | 128/24 A |
| 3,973,150 | 8/1976 | Tamura | 310/334 |
| 3,990,452 | 11/1976 | Murry et al. | 128/305 |
| 4,504,264 | 3/1985 | Kelman | 604/22 |

FOREIGN PATENT DOCUMENTS

| | | | |
|---|---|---|---|
| 1068924 | 11/1959 | Fed. Rep. of Germany | 128/24 A |
| 2418631 | 10/1975 | Fed. Rep. of Germany | 128/24 A |
| 1069323 | 2/1954 | France | 128/24 A |

*Primary Examiner*—Clyde I. Coughenour
*Attorney, Agent, or Firm*—Hill, Van Santen, Steadman & Simpson

[57] ABSTRACT

A vented ultrasonic transducer for a medical handpiece which is provided with a number of vents which extend from the interior mounted crystal drive motor to the rear end of the handpiece so as to allow the handpiece to be rapidly sterilized with a flash autoclave and the vent tubes allow moisture to pass in and out of the handpiece and prevent moisture from remaining in the handpiece and shorting out the crystal electrical drive after sterilization has been completed.

6 Claims, 1 Drawing Sheet

VENTED ULTRASONIC TRANSDUCER FOR SURGICAL HANDPIECE

BACKGROUND OF THE INVENTION

1. Field of the Invention

This invention relates in general to ultrasonic handpiece which is vented so as to prevent moisture from shorting out the electrical leads during sterilization of the device.

2. Description of the Prior Art

U.S. Pat. No. 3,990,452 assigned to the assignee of the present invention discloses an ultrasonic handpiece which has crystals that are electrically driven to energize the handpiece and a working tool such as a cutting needle mounted to the handpiece. When a surgeon desires to use an ultrasonic handpiece to perform a number of operations one right after another, it is necessary to flash autoclave the handpiece so as to sterilize it between operations. Such flash autoclave provides for a rapid sterilization of the handpiece as, for example, in a seven minute cycle. Handpieces according to the prior art when subjected to flash autoclave have been subject to shorting of the electrical drive system to the crystals in the handpiece due to condensation of moisture within the handpiece.

SUMMARY OF THE INVENTION

The present invention provides for one or more vents which extend into the interior of a surgical ultrasonic handpiece so as to allow moisture to pass in and out of the handpiece during flash autoclave and thus prevents moisture from remaining in the handpiece and thus to prevent shorting out of the crystal electrical drive after sterilization of the handpiece has been accomplished.

A feature of the present invention is the provision of vent tubes which extend into the interior of the handpiece so as to allow the passage of moisture into and out of the handpiece during rapid sterilization of the handpiece so as to prevent shorting of the electrical drive system of the handpiece.

Other objects, features and advantages of the invention will be readily apparent from the following description of certain preferred embodiments thereof taken in conjunction with the accompanying drawings although variations and modifications may be effected without departing from the spirit and scope of the concepts of the disclosure and in which:

DESCRIPTION OF THE PREFERRED EMBODIMENTS

Figure 1:
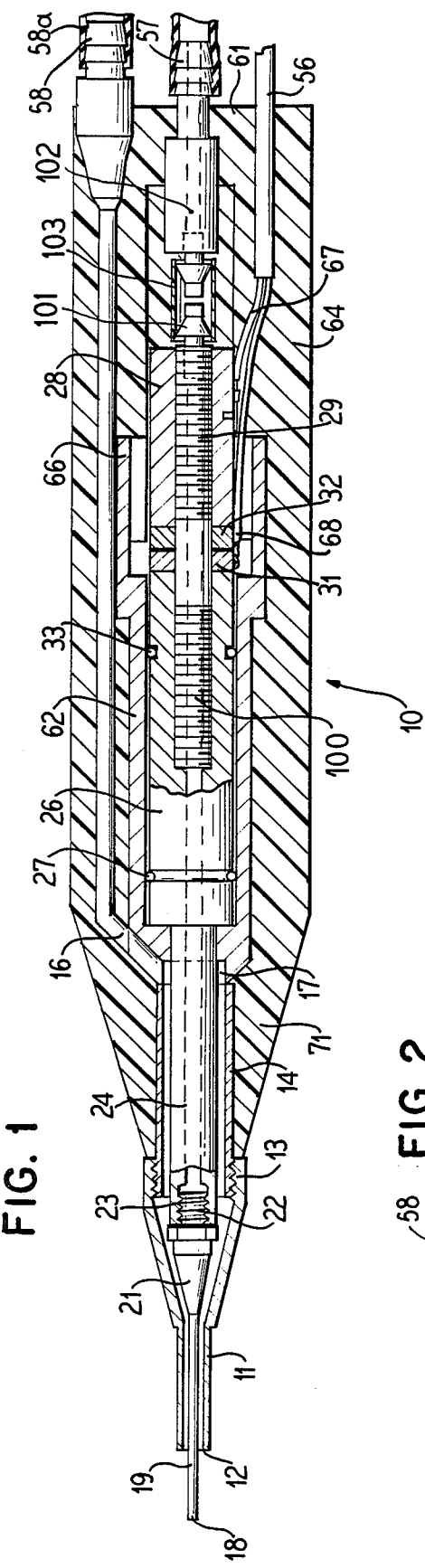
FIG. 1 is a partially sectional view of an ultrasonic handpiece according to the invention.
Figure 2:
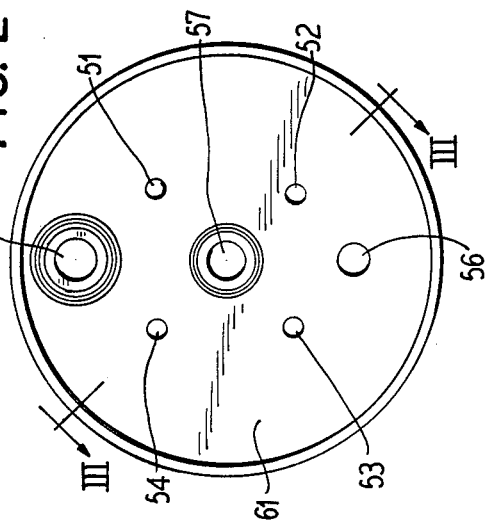
FIG. 2 is a rear view of the handpiece illustrated in FIG. 1.

The FIGS. illustrate the handpiece 10 which has its left end relative to FIG. 1 has an irrigation sleeve 11 formed with the central opening 12 through which irrigation fluid can be supplied to an operation site. The irrigation sleeve 11 has an enlarged internally threaded portion 13 that is threadedly received on a hollow shell 14 that extends into the handpiece and connects to a shell 62 of larger diameter which receives therein a front piece 26 of titanium and is generally of cylindrical-shape and is formed with a central opening. A pair of O-rings 27 and 33 are mounted in the front piece 26 in grooves so as to provide a fluid seal between the front piece 26 and the enlarged shell portion 62. An irrigation tube 16 communicates with the space within the irrigation sleeve 11 so as to provide irrigation fluid therethrough. The tube 16 terminates in a nipple 58 at the rear end of the handpiece to which an irrigation supply tube 58a can be attached. An operating needle 19 has a point 18 and has a transition portion 21 which is connected by external threads 22 to a threaded sleeve 23 which has an internal opening that mates with an internal opening through the front piece 26 and passes through the crystals 31 and 32 and the cylindrical rear piece 28 which is formed with a central opening to allow aspiration therethrough. An aspiration tube 57 is connected by suitable coupling means to the passageway through the crystals 31, 32 and the front piece 26 and rear piece 28 to the needle so as to aspirate through the opening of the needle.

A hollow threaded stud 100 is receivable in mating threads in the front piece 26 and has threads 29 receivable in mating threads in the rear piece 28 so as to hold the assembly together. The aspiration passage passes through the stud 100 and adaptor 101 is mounted therein. A holding sleeve 103 connects the rear end of the aspiration line. 57 is the aspiration output fitting.

Figure 3:
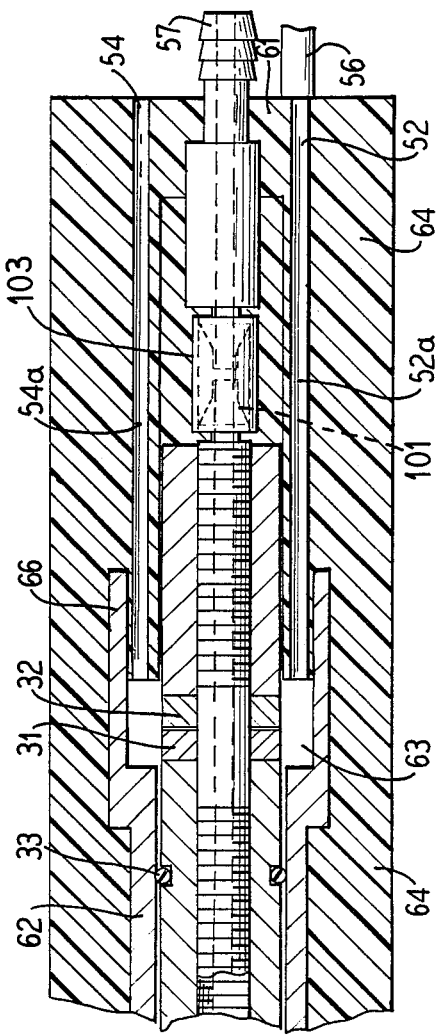
FIG. 3 is a partially cutaway sectional view taken on III—III from FIG. 2.

A number of ventilation tubes as, for example, four which as designated by numerals 51, 52, 53 and 54 extend from the rear end 61 of the handpiece to the space 63 between the crystals 31 and 32 as illustrated in FIG. 3. The handpiece is surrounded by suitable sealing material 64 of generally cylindrical-shape and which has a rear portion 61 which seals the rear end of the handpiece. It also has a tapered generally conical portion 71 which forms the front end of the handpiece as illustrated in FIG. 1.

When the handpiece is to be used in an operation it must be sterilized and so-called flash autoclave sterilization is often used for such sterilization. In such rapid sterilization, the sterilization occurs in a seven minute cycle and in prior art devices moisture has passed through the O-ring seals 27 and 33 and other openings of the handpiece such that moisture condenses in the inside of the crystals and shorts out the electrical drive system of the crystals. The electrical drive system is provided with an electrical lead 56 which enters the rear portion 61 of the handpiece and has a first lead 67 which provides a ground wire and one or more other leads 68 which are connected to the crystals 31 and 32 to cause both of them to oscillate. With prior art devices when the rapid sterilization occurs with flash autoclave, the handpiece is rendered inoperative due to moisture condensation which shorts out the electrical leads to the crystals. With the present invention, the four vent tubes 51, 52, 53 and 54 provide direct open passageways from the end 61 of the handpiece into the space surrounding the crystals 31 and 32 and the electrical leads and provides open passageways for moisture to pass from the space between the crystals 31 and 32 to outside of the confines of the handpiece during the rapid sterilization.

It has been observed that handpieces according to the invention can be rapidly sterilized and used by the surgeon as soon as sterilization has been completed and there is no shorting or contamination of the electrical drive system as in prior art handpieces.

Although the invention has been described with respect to preferred embodiments, it is not to be so limited as changes and modifications can be made which are within the full intended scope of the invention as defined by the appended claims.

We claim as our invention:

1. An ultrasonic handpiece for surgical operations comprising, a generally cylindrical-shaped housing, an electrical power system including an ultrasonic motor comprising a pair of side-by-side electrically driven crystals and electrical leads mounted in said housing, a surgical tool which must be periodically sterilized with steam or hot moisture having one end connected to said motor and with the other end extending from said housing, first and one or more than other said electrical power leads extending into said housing and said first electrical power lead connected to ground and said one or more other electrical power leads connected to the electrically driven crystals, and at least one vent tube extending through said housing with one end terminating adjacent said side-by-side crystals and power leads of said motor and the other end extending through housing so as to provide a path for removing moisture deposited during sterilization from the inside of said housing so as to prevent said first and one or more other electrical power leads and crystals from being shorted by moisture which would provide an electrical path within said electrical power system which would prevent operation.

2. An ultrasonic handpiece according to claim 1 including an aspiration passageway formed from said surgical tool through said housing.

3. An ultrasonic handpiece according to claim 2 including a sleeve attached to said housing and extending to said surgical tool and an irrigation passage extending through said housing to said sleeve.

4. An ultrasonic handpiece according to claim 1 including a plurality of vent tubes extending through said housing with first ends terminating adjacent said motor and second ends extending through said housing.

5. An ultrasonic handpiece according to claim 1 including a removeable cap mountable over said other end of said vent tube.

6. An ultrasonic handpiece according to claim 1 including a valve mounted in said vent tube.

* * * * *